United States Patent
Heni et al.

(10) Patent No.: US 10,791,322 B2
(45) Date of Patent: Sep. 29, 2020

(54) APPARATUS FOR CAPTURING A STEREO IMAGE

(71) Applicant: Karl Storz SE & Co. KG, Tuttlingen (DE)

(72) Inventors: Andreas Heni, Tuttlingen (DE); Markus Kupferschmid, Tuttlingen (DE); Lawrence Natusch, Tuttlingen (DE); Daniel Ulmschneider, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 43 days.

(21) Appl. No.: 15/903,827

(22) Filed: Feb. 23, 2018

(65) Prior Publication Data

US 2018/0241987 A1    Aug. 23, 2018

(30) Foreign Application Priority Data

Feb. 23, 2017   (DE) .................. 10 2017 103 721

(51) Int. Cl.
| | |
|---|---|
| *H04N 13/282* | (2018.01) |
| *A61B 1/00* | (2006.01) |
| *G02B 23/24* | (2006.01) |
| *H04N 5/232* | (2006.01) |

(52) U.S. Cl.
CPC ....... *H04N 13/282* (2018.05); *A61B 1/00179* (2013.01); *A61B 1/00183* (2013.01); *A61B 1/00193* (2013.01); *G02B 23/2415* (2013.01); *H04N 5/23296* (2013.01)

(58) Field of Classification Search
CPC ............ A61B 1/00193; A61B 1/00179; A61B 1/00183; H04N 5/23296; H04N 13/282; G02B 23/2415
See application file for complete search history.

(56) References Cited

U.S. PATENT DOCUMENTS

| | | | | |
|---|---|---|---|---|
| 3,583,801 | A | * | 6/1971 | Roth .................. G03B 1/22 352/173 |
| 3,901,220 | A | * | 8/1975 | Koyasu ............. A61B 1/00165 600/176 |
| 3,994,557 | A | * | 11/1976 | Hopkins ............... A61B 1/307 359/374 |
| 4,059,336 | A | * | 11/1977 | Hopkins ............... G02B 21/04 359/366 |

(Continued)

FOREIGN PATENT DOCUMENTS

| | | | |
|---|---|---|---|
| DE | 4138191 A1 * | 5/1993 | ............. B21C 47/10 |
| DE | 102010041857 A1 | 4/2012 | |
| GB | 758451 | * 8/1954 | |

*Primary Examiner* — Philip P. Dang (74) *Attorney, Agent, or Firm* — Whitmyer IP Group LLC (57) ABSTRACT

An apparatus for capturing a stereo image includes a first objective for producing a first image, a second eye objective for producing a second eye image, a first viewing direction device rotatable about a first axis assigned the first objective, and a second viewing direction device rotatable about a second axis assigned the second objective. The viewing direction of the apparatus is rotatable by simultaneous rotation of the first and second viewing direction devices. The first objective or part is movable in a translational fashion. A cam mechanism is provided and embodied to couple a rotation of the first viewing direction device to a translational movement of the first objective or part.

19 Claims, 5 Drawing Sheets

(56) References Cited

U.S. PATENT DOCUMENTS

| | | | | |
|---|---|---|---|---|
| 4,091,397 A * | 5/1978 | Gulbrandsen | G03B 17/53 | 396/2 |
| 4,138,191 A * | 2/1979 | Peyman | G02B 21/0012 | 359/363 |
| 4,361,387 A * | 11/1982 | Cloutier | G03B 7/0807 | 396/263 |
| 4,448,498 A * | 5/1984 | Muller | G02B 21/20 | 359/363 |
| 4,651,201 A * | 3/1987 | Schoolman | A61B 1/00048 | 348/45 |
| 4,844,071 A * | 7/1989 | Chen | A61B 1/042 | 600/112 |
| 4,948,235 A * | 8/1990 | Akitake | G02B 7/10 | 359/700 |
| 5,061,995 A * | 10/1991 | Lia | A61B 1/07 | 348/68 |
| 5,122,650 A * | 6/1992 | McKinley | A61B 1/00193 | 250/208.1 |
| 5,976,071 A * | 11/1999 | Sekiya | A61B 1/00193 | 600/111 |
| 5,976,076 A * | 11/1999 | Kolff | A61B 1/00177 | 600/111 |
| 6,111,582 A * | 8/2000 | Jenkins | G06T 15/40 | 345/421 |
| 6,219,182 B1 * | 4/2001 | McKinley | G02B 7/16 | 359/400 |
| 6,396,627 B1 * | 5/2002 | Tachihara | G02B 21/22 | 348/42 |
| 6,409,658 B1 * | 6/2002 | Mitsumori | A61B 1/00096 | 600/130 |
| 6,517,206 B2 * | 2/2003 | Shevlin | G02B 26/0825 | 351/209 |
| 6,582,358 B2 * | 6/2003 | Akui | A61B 1/00183 | 600/111 |
| 6,626,828 B2 * | 9/2003 | Dohi | A61B 1/00183 | 600/171 |
| 6,641,530 B2 * | 11/2003 | Mitsumori | A61B 1/00096 | 600/130 |
| 7,156,863 B2 * | 1/2007 | Sonnenschein | A61B 1/0005 | 227/181.1 |
| 7,212,330 B2 * | 5/2007 | Seo | G06K 9/209 | 356/601 |
| 7,805,386 B2 * | 9/2010 | Greer | G06N 3/04 | 706/12 |
| 7,848,791 B2 * | 12/2010 | Schmitt | A61B 5/0066 | 356/497 |
| 7,909,463 B2 * | 3/2011 | Dick | A61B 3/14 | 351/206 |
| 8,038,230 B2 * | 10/2011 | Nakamura | B60T 8/3225 | 303/116.4 |
| 8,179,597 B2 * | 5/2012 | Namba | G01N 21/6458 | 359/383 |
| 8,433,221 B2 * | 4/2013 | Minbe | G03G 15/2032 | 399/121 |
| 9,199,168 B2 * | 12/2015 | Ito | A63F 13/428 | |
| 9,333,042 B2 * | 5/2016 | Diolaiti | A61B 1/00087 | |
| 9,642,606 B2 * | 5/2017 | Charles | A61B 1/32 | |
| 9,754,411 B2 * | 9/2017 | Geller | G06T 11/003 | |
| 9,782,159 B2 * | 10/2017 | Tesar | A61B 1/05 | |
| 9,815,307 B2 * | 11/2017 | Mueller | B41J 11/0095 | |
| 9,910,482 B2 * | 3/2018 | Brunolli | H04L 25/0278 | |
| 9,916,538 B2 * | 3/2018 | Zadeh | G06N 7/005 | |
| 9,936,863 B2 * | 4/2018 | Tesar | A61B 1/05 | |
| 10,192,135 B2 * | 1/2019 | Krenzer | G06K 9/00335 | |
| 2006/0020172 A1 * | 1/2006 | Luerssen | A61B 1/2673 | 600/188 |
| 2007/0030446 A1 * | 2/2007 | Su | A61F 9/008 | 351/205 |
| 2013/0293939 A1 * | 11/2013 | Rotschild | G02B 27/2271 | 359/9 |
| 2013/0310648 A1 | 11/2013 | Kazakevich et al. | | |
| 2014/0063485 A1 * | 3/2014 | Palmieri | G01N 21/87 | 356/30 |
| 2014/0066700 A1 * | 3/2014 | Wilson | A61B 1/00045 | 600/102 |
| 2014/0066701 A1 * | 3/2014 | Wilson | A61B 1/00009 | 600/102 |
| 2014/0357951 A1 * | 12/2014 | Muller | G02B 23/2415 | 600/111 |
| 2015/0097827 A1 * | 4/2015 | Cohen | G06T 5/005 | 345/420 |
| 2017/0143442 A1 * | 5/2017 | Tesar | A61B 90/37 | |
| 2017/0234071 A1 * | 8/2017 | Spatz | E21B 7/06 | 175/61 |
| 2018/0042641 A1 * | 2/2018 | Govari | A61B 17/320758 | |

* cited by examiner

APPARATUS FOR CAPTURING A STEREO IMAGE

TECHNICAL FIELD

The present invention relates to an apparatus for capturing a stereo image, which facilitates pivoting or rotating of the viewing direction.

BACKGROUND

DE 10 2010 041 857 A1 describes a stereo endoscope having a lateral or oblique viewing direction, i.e. a viewing direction that deviates from a central 0° viewing direction. The lateral viewing direction is determined by distal deflection elements (paragraph [0024]). The viewing direction is changed by rotating the distal deflection elements (paragraph [0024]). An inclined distal viewing window, the distal deflection elements being arranged therebehind, is also rotated (paragraph [0026]). The distal deflection elements carry out movements with a same direction, with there being no change in the axial distance between the image sensor and the deflection element during the rotation (paragraph [0027]). Each image sensor is movable in the axial direction together with the assigned deflection element (paragraph [0029]).

US 2013/0310648 A1 (also published as U.S. Pat. No. 9,204,787 B2) describes a stereo endoscope with a pivotable viewing direction. The endoscope has two optical channels which are rotated about their axes in synchronous fashion and, at the same time, displaced in a synchronous and opposite fashion in a manner parallel to their axes.

SUMMARY

An object of the present invention consists in developing an improved apparatus for capturing a stereo image which, in particular, allows a rotation of the viewing direction on a conical envelope without a rotation of the base.

This object is achieved by the subject matter of the independent claims.

Developments are specified in the dependent claims.

An apparatus for capturing a stereo image comprises a first objective for producing a first image that is intended to be observed by a first eye of an observer, a second objective for producing a second image that is intended to be observed by a second eye of an observer, a first viewing direction device that is rotatable about a first axis of rotation and assigned to the first objective, and a second viewing direction device that is rotatable about a second axis of rotation and assigned to the second objective, wherein the viewing direction of the apparatus is rotatable by way of the simultaneous rotation of the first viewing direction device about the first axis of rotation and the second viewing direction device about the second axis of rotation, wherein the first objective or part of the first objective is movable in a translational fashion, and wherein a cam mechanism is provided and embodied to couple a rotation of the first viewing direction device to a translational movement of the first objective or of part of the first objective.

An apparatus for capturing a stereo image comprises a first objective for producing a first image that is intended to be observed by a first eye of an observer, a second objective for producing a second image that is intended to be observed by a right eye of an observer, a first viewing direction device that is rotatable about a first axis of rotation and assigned to the first objective, a second viewing direction device that is rotatable about a second axis of rotation and assigned to the second objective, a first image sensor for capturing the first image, and a second image sensor for capturing the second image, wherein the viewing direction of the apparatus is rotatable by way of the simultaneous rotation of the first viewing direction device about the first axis of rotation and the second viewing direction device about the second axis of rotation, wherein the first objective or part of the first objective is movable in a translational fashion, and wherein a cam mechanism is provided and embodied to couple a rotation of the first viewing direction device to a translational movement of the first objective or of part of the first objective.

In particular, the apparatus is a stereo endoscope or stereo exoscope for medical or non-medical applications.

In particular, the first objective and the second objective are of identical construction. The first image produced by the first objective and the second image produced by the second objective can be converted into analog or digital image signals by the assigned image sensors, said image signals being amplified, filtered, prepared, processed, stored and/or being able to control a reproduction at a display apparatus. The image sensors can be arranged immediately proximally to the assigned objectives in order to immediately capture the images produced by the objectives. Alternatively, a rod lens system or any other relay lens system or a coherent bundle of optical fibers can be assigned to each objective in order to facilitate an optical transfer of the image produced by the objective to a proximal end of the apparatus, for example.

In particular, both viewing direction devices are of identical construction. In particular, each viewing direction device comprises one or more reflective plane or curved faces, for example within, or at, a prism or between a plurality of prisms.

The first viewing direction device and the first objective are part of a first beam path. The optical axis of the first beam path, referred to below as first optical axis, has one or more kinks as a result of the first viewing direction device, and so the first optical axis has different directions on the distal and proximal side of the viewing direction device. Light-refracting interfaces at or between lens elements of the first objective are, in particular, rotationally symmetric in relation to the first optical axis. Below, a distinction is made between a distal portion and a proximal portion of the first optical axis. The distal portion of the first optical axis is the portion of the first optical axis situated distally from the first viewing direction device. The proximal portion of the first optical axis is the portion of the first optical axis situated proximally from the first viewing direction device.

The second viewing direction device and the second objective are part of a second beam path. The optical axis of the second beam path, referred to below as second optical axis, has one or more kinks as a result of the first viewing direction device, and so the second optical axis has different directions on the distal and proximal side of the viewing direction device. Light-refracting interfaces at or between lens elements of the second objective are, in particular, rotationally symmetric in relation to the second optical axis. Below, a distinction is made between a distal portion and a proximal portion of the second optical axis. The distal portion of the second optical axis is the portion of the second optical axis situated distally from the second viewing direction device. The proximal portion of the second optical axis is the portion of the second optical axis situated proximally from the second viewing direction device.

The first viewing direction device can be arranged distally from the first objective and separately from the first objective. In this case, in particular, all light-refracting interfaces of the first objective are rotationally symmetric in relation to the proximal portion of the first optical axis. Here, the apparatus can be provided and embodied to only move, but not rotate, the first objective in a translational fashion (for example together with an assigned image sensor in order to keep the image distance constant), depending on the rotational position of the first viewing direction device.

Alternatively, the apparatus can be embodied to rotate the first objective together with the first viewing direction device. Here, in particular, the first viewing direction device and the first objective can be rigidly connected to one another or form a common component and/or be partly or completely integrated.

Alternatively, the first objective, in part or in the entirety thereof, can be provided and arranged distally from the first viewing direction device. Here, in particular, all or some of the light-refracting interfaces of the first objective are rotationally symmetric in relation to the distal portion of the first optical axis. In this case, the first viewing direction device and the first objective are rotated together about the first axis of rotation and are moved in translational fashion in the process.

In particular, the first axis of rotation corresponds to the proximal portion of the first optical axis. The direction of the translational movability of the first objective and, optionally, of the first viewing direction device is parallel to the first axis of rotation, in particular, and hence parallel to the proximal portion of the first optical axis.

Statements that are largely or completely the same apply, in particular, to the second viewing direction device and the second beam path.

In particular, the second objective may also be movable in a translational fashion. In this way, a further cam mechanism can be provided and embodied to couple a rotation of the second viewing direction device to a translational movement of the second objective. The cam mechanism and the further cam mechanism are embodied in such a way, in particular, that the translational movement of the first objective and the translational movement of the second objective are in the opposite direction at all times. Alternatively, provision can be made of only one cam mechanism, which couples the rotation of the first viewing direction device to the translational movement of the first objective, while the second objective is unmoved or at least not moved in a translational fashion (i.e., in particular, not at all or only in a rotational fashion).

The viewing direction of the first beam path is the direction in which a faraway object lies in relation to the distal end of the apparatus when said object is imaged in the center of the first image. The viewing direction of the second beam path is the direction in which a faraway object lies in relation to the distal end of the apparatus when said object is imaged in the center of the second image. The viewing direction of the apparatus is the direction in which a faraway object or an object at a predetermined distance lies in relation to the distal end of the apparatus when said object is imaged in the center of the first image and in the center of the second image.

The first viewing direction device and the second viewing direction device are rotationally coupled to one another in such a way that, in particular, the viewing directions of the two viewing direction devices are parallel at all times and correspond to a single common viewing direction of the apparatus. Alternatively, the first viewing direction device and the second viewing direction device can be coupled in such a way that, for example, the viewing directions of both beam paths intersect one another at all times at a predetermined distance from the distal end of the apparatus.

By way of example, the proximal portion of the first optical axis intersects the first image sensor in the center thereof or in the center of the image captured by the first image sensor, and the proximal portion of the second optical axis intersects the second image sensor in the center thereof or in the center of the image captured by the second image sensor. In this case, in particular, the direction of the distal portion of the first optical axis is the viewing direction of the first beam path and the direction of the distal portion of the second optical axis is the viewing direction of the second beam path. In particular, the movement of the first viewing direction device and the movement of the second viewing direction device are coupled in such a way that the distal portions of the first optical axis and of the second optical axis, and hence the first viewing direction and the second viewing direction, are parallel at all times. Alternatively, the movement of the first viewing direction device and the movement of the second viewing direction device may be coupled in such a way that, for example, the distal portions of the first optical axis and of the second optical axis intersect one another at all times at a predetermined distance.

In particular, the viewing direction of the apparatus is rotatable on a conical envelope, wherein the axis of symmetry of the conical envelope corresponds, or is parallel, to the axis of symmetry of the distal end of a shaft of the apparatus. Half of the aperture angle of the conical envelope corresponds to the angle through which each viewing direction device refracts the viewing direction or the optical axis of the assigned beam path. This angle may be respectively constant, i.e. unchangeable, for both viewing direction devices, or it may be simultaneously changeable for both viewing direction devices.

The viewing direction can be rotated on a conical envelope by virtue of the apparatus being rotated about the longitudinal axis of the shaft, even in a conventional apparatus for capturing a stereo image in which the viewing direction is not parallel to the longitudinal axis of a shaft of the apparatus. However, the image sensors and the base, i.e. the direction of the connecting path between the centers of the two image sensors, are also rotated in the process. Hence, a stereo image captured with this conventional apparatus likewise rotates, quickly leading to a loss of orientation and possibly at least making the guidance of medical instruments much more difficult. The two images could each be rotated back by digital means such that top and bottom, left and right are maintained in the reproduced stereo image. However, it would not be possible to eliminate the rotation of the base and this would lead to a destruction of the spatial perception.

In contrast to such a conventional apparatus, the rotation of the viewing direction devices of the apparatus described here facilitates a rotation of the viewing directions without a rotation of the image sensors and without a rotation of the base.

The cam mechanism facilitates simple and reliable coupling of the rotation of the first viewing direction device to a translational movement of the first objective. What this can achieve is that the object distance, and hence also the imaging scale, is the same or substantially the same for both beam paths, independently of the set viewing direction for objects in the set viewing direction.

In particular, in the case of an apparatus as described here, the cam mechanism or a further cam mechanism is provided and embodied to couple a rotation of the first viewing direction device to a translational movement of the first viewing direction device in the direction in which the first objective or part of the first objective is movable.

If the first objective and the first viewing direction device are integrated or form a common component or are rigidly connected to one another or connected to one another in such a way that they are only rotatable relative to one another about the first axis of rotation, the cam mechanism can bring about a simultaneous translational movement of the first viewing direction device and the first objective. If the first viewing direction device and the first objective are not connected to one another, a first cam mechanism can couple the rotation of the first viewing direction device to the translational movement of the first objective and a second cam mechanism can couple the rotation of the first viewing direction device to the translational movement of the first viewing direction device.

In particular, an apparatus, as described here, further comprises a further cam mechanism provided and embodied to couple a rotation of the first viewing direction device to a translational movement of the first viewing direction device in the direction in which the first objective is movable, wherein the further cam mechanism is provided and embodied to move the first viewing direction device in a translational fashion within a range that is smaller than the range within which the cam mechanism moves the first objective in a translational fashion.

Particularly if the refractive power of the first viewing direction device is zero or significantly smaller than the remaining constituent parts of the first beam path (i.e., the focal length of the first viewing direction device is infinite or very much larger than the focal length of the remaining constituent parts of the first beam path), the translational position of the first viewing direction device has no or only a little influence on the position of the first image. In this case, the first viewing direction device can be moved less than the first objective, or even not at all, without influencing the position of the first image.

Moving the first viewing direction device within a smaller range, and hence less far, than the first objective, or even not moving it at all, may reduce or prevent partial shadowing by the edge of a window component at the distal end of the apparatus.

Moving the first viewing direction device within a smaller range, and hence less far, than the first objective may prevent a variation, dependent on the viewing direction, of the width of the base, i.e. the distance between the distal portions of the optical axes. In the case of a stereo endoscope or stereo exoscope or any apparatus for capturing a stereo image with two straight and parallel beam paths, the base is the straight line between the centers of the two image sensors and the distance between the optical axes. In the case, present here, of an apparatus for capturing a stereo image with angled or kinked beam paths, the base is the distance between the distal portions of the optical axes provided the optical axes are parallel there. In the case of non-parallel optical axes, the base is the distance between the distal portions of the optical axes at the entrance pupils of the two beam paths.

In particular, in the case of an apparatus, as described here, the cam mechanism or a further cam mechanism is provided and embodied to couple a rotation of the first viewing direction device to a translational movement of the first image sensor that is assigned to the first objective or to a light entry face of an image transmission device.

The first objective and a first image sensor assigned to the first objective or the first objective and a light entry face of an image transmission device assigned to the first objective can be connected to one another in a mechanically rigid fashion or can be connected to one another in such a way that the first objective can only be rotated relative to the assigned image sensor or relative to the light entry face of the assigned image transmission device. In this case, a single cam mechanism is sufficient to also couple a translational movement of the first image sensor assigned to the first objective or of the light entry face of the image transmission device assigned to the first objective to a rotation of the first viewing direction device.

If the first objective is not directly mechanically coupled to the assigned first image sensor or the light entry face of an assigned image transmission device, a first cam mechanism can couple a translational movement of the first objective to a rotation of the first viewing direction device and a second cam mechanism can couple a translational movement of the first image sensor assigned to the first objective or of a light entry face of an image transmission device assigned to the first objective to a rotation of the first viewing direction device.

By virtue of keeping the image distance, i.e., the distance between the first objective and the first image sensor, constant, the focusing remains constant, i.e., the distance at which objects that are imaged in focus on the first image sensor lie remains unchanged, independently of the set viewing direction.

In particular, in the case of an apparatus, as described here, the first objective comprises a first part and a second part, wherein the apparatus is embodied in such a way that, either, only the translational movement of the first part is coupled to the rotation of the first viewing direction device or that a rotation of the first viewing direction device is accompanied by different translational movements of the first part and of the second part of the first objective.

In particular, the first part is directly or indirectly (via the cam mechanism) coupled to the first viewing direction device in such a way that a rotation of the first viewing direction device is accompanied by synchronous translational movements of the viewing direction device and of the first part of the first objective. Here, the second part of the first objective may be at rest in particular together with the first image sensor or it may carry out a different translational movement, for example with a lower speed and over a shorter path. In particular, the location of the second part of the first objective and the location of the first image sensor are independent of the rotational position of the first viewing direction device.

In particular, the first part of the first objective is arranged distally from the second part. The first part and the second part of the first objective are embodied in such a way that, in particular, the light emanating from an object, which is ultimately imaged on the first image sensor in focus, extends parallel or substantially parallel between the first part and the second part of the objective.

In particular, an apparatus, as described here, further comprises a drive shaft that is rotationally coupled to the first viewing direction device and to the second viewing direction device.

The rotational coupling of the viewing direction devices to a drive shaft facilitates the rotation of the viewing direction devices and hence of the viewing direction of the apparatus by way of rotating the drive shaft. Thus, the drive shaft facilitates the mechanical control of the viewing direction.

In particular, the drive shaft and the viewing direction devices are rotationally coupled to one another by way of gears. By way of example, teeth are provided at the outer circumferences of mounts of the viewing direction devices, said teeth forming gears. In particular, the gears at the viewing direction devices have the same size; a gear at the drive shaft, which meshes with the gears at the viewing direction devices, may have a smaller or larger diameter in order to bring about a step-down or step-up gear ratio.

In particular, in the case of an apparatus, as described here, at least either the first viewing direction device and the second viewing direction device are in each case arranged, at least in part, next to the drive shaft, or the first objective and the second objective are in each case arranged, at least in part, next to the drive shaft.

In particular, the proximal portion of the first optical axis of the first beam path and the proximal portion of the second optical axis of the second beam path are respectively arranged next to the drive shaft or next to the distal end of the drive shaft.

Thus, in particular, the drive shaft is not a hollow shaft, with the beam paths arranged in the interior thereof. In the case of a hollow shaft, within which the beam paths are arranged, the diameter of the installation space available for the beam paths shrinks by at least twice the wall thickness of the hollow shaft. In comparison thereto, more installation space may be available for the beam paths when arranging the viewing direction devices next to the drive shaft or next to the distal end thereof. In particular, the drive shaft is arranged, at least in part, between the viewing direction devices.

In particular, in the case of an apparatus, as described here, the drive shaft comprises a cam carrier, which is a constituent part of the cam mechanism, or said drive shaft is rotationally coupled to a cam carrier, which is a constituent part of the cam mechanism, wherein a cam, which is a constituent part of the cam mechanism, for coupling a rotation of the first viewing direction device to a translational movement of the first objective or part of the first objective is provided on the outer side of the cam carrier.

By way of example, the cam is embodied as a groove, web or step on the cam carrier. The cam carrier can be embodied as a gear for rotational coupling to the viewing direction devices at the same time. A plurality of cams may be provided on the cam carrier, for example respectively one cam for each objective (or respectively one part of each objective) and/or respectively one cam for each viewing direction device and/or respectively one cam for each image sensor. Each cam can couple the rotation of the cam carrier and hence indirectly the rotation of the viewing direction devices to a translational movement of an assigned objective (or of part of the assigned objective) or of an assigned viewing direction device or of an assigned image sensor. By virtue of providing different cams, it is possible, for example, to move both objectives (or parts of both objectives) counter to one another and/or move the two viewing direction devices counter to one another and/or move the two image sensors counter to one another. Further, various cams may have different gradients or leads, in order, for example, to move one viewing direction device less strongly than the assigned objective (or part of the assigned objective) and the assigned image sensor.

In particular, in the case of an apparatus, as described here, the cam mechanism comprises a groove or a web or a step at the drive shaft or at a cam carrier that is rotationally coupled to the drive shaft and a pin or a web or any other sensing device at the first objective or part of the first objective or at a component that is translationally coupled to the first objective or part of the first objective.

In particular, in the case of an apparatus, as described here, the cam mechanism comprises a groove or a web or a step at the first objective or part of the first objective or at a component that is translationally coupled to the first objective or part of the first objective and a sensing device at the drive shaft or at a component that is rotationally coupled to the drive shaft.

Thus, the drive shaft can simultaneously serve for the rotation of the viewing direction devices and be a constituent part of the cam mechanism for coupling the translational movement of the first objective (or part of the first objective) to the rotational movement of the first viewing direction device. This may facilitate a compact structure of the apparatus.

In particular, in the case of an apparatus, as described here, the drive shaft is arranged between the first objective and the second objective.

In particular, the optical axes of the objectives, which are the proximal portions of the optical axes of the beam paths in this case, and the axis of rotation of the drive shaft lie in a plane, wherein the distances of the axis of rotation of the drive shaft from the optical axes of the objectives can be the same.

Alternatively, the axis of rotation of the drive shaft does not lie in the plane in which the optical axes of the objectives or the proximal portions of the optical axes of the beam paths lie. Nevertheless, the distances of the axis of rotation of the drive shaft from the proximal portions of the optical axes of the beam paths can be the same in this case. Arranging the drive shaft not between the objectives, but with a lateral offset, can save installation space and consequently facilitate more installation space for the objectives and other components.

In particular, an apparatus, as described here, further comprises a shaft having a distal end, wherein the outer lateral face of the shaft is rotationally symmetric in relation to an axis of symmetry, at least in the vicinity of the distal end of the shaft, wherein the first viewing direction device, the second viewing direction device, the first objective and the second objective are arranged in the shaft, and wherein, at least in one viewing direction of the apparatus, a proximal portion of the optical axis of the first viewing direction device and a proximal portion of the optical axis of the second viewing direction device are not arranged mirror symmetrically in relation to a plane of symmetry that contains the axis of symmetry of the shaft.

The first viewing direction device, the second viewing direction device, the first objective, and the second objective are arranged in the shaft, in particular in the vicinity of the distal end of the shaft. The optical axes of the viewing direction devices at the proximal ends thereof are in particular not spaced apart from the axis of symmetry of the outer lateral face of the shaft to the same extent, at least in the case of one viewing direction. Alternatively, the optical axes of the viewing direction devices at the proximal ends thereof and the axis of symmetry of the outer lateral face of the shaft do not lie in a plane, at least in the case of one viewing direction.

Such a non-mirror-symmetrical arrangement can prevent or reduce shadowing by an edge of a window component at the distal end of the shaft.

In particular, an apparatus, as described here, further comprises a device for the translational movement of the viewing direction devices in a direction orthogonal to the axis of symmetry of the shaft, depending on the set viewing direction.

The viewing direction devices and, together therewith, in particular the objectives and the image sensors as well can be displaced along a straight path or moved on orbits or other non-straight trajectories (in each case in relation to a sectional plane orthogonal to the proximal portions of the optical axes and orthogonal to the axis of symmetry of the shaft), depending on the set viewing direction. Presented in a simplified manner, the viewing direction devices and, in particular, the whole beam paths are e.g. moved to the left when the viewing direction goes to the right, and moved to the right when the viewing direction goes to the left. Optionally, the viewing direction devices and, in particular, the whole beam paths can be moved downward when the viewing direction goes upward, and upward when the viewing direction goes downward. This can reduce or prevent the shadowing by the edge of a window component.

In particular, in the case of an apparatus, as described here, each of the two viewing direction devices are embodied in such a way that, in relation to a projection parallel to the proximal portion of the optical axis of the image viewing device, the point of intersection of the distal portion of the optical axis of the viewing direction device with the light entry face of the viewing direction device lies outside of the cross section of the viewing direction device at the proximal end thereof.

Expressed differently, the viewing direction device offsets the optical axis between the light entry face at the distal end and the light exit face at the proximal end by more than half the diameter of the viewing direction device at the proximal end thereof. This offset may prevent or reduce shadowing by the edge of a transparent window component at the distal end of the apparatus.

BRIEF DESCRIPTION OF THE DRAWINGS

Embodiments are explained in more detail below on the basis of the attached figures. In the figures.

DETAILED DESCRIPTION

Figure 1:
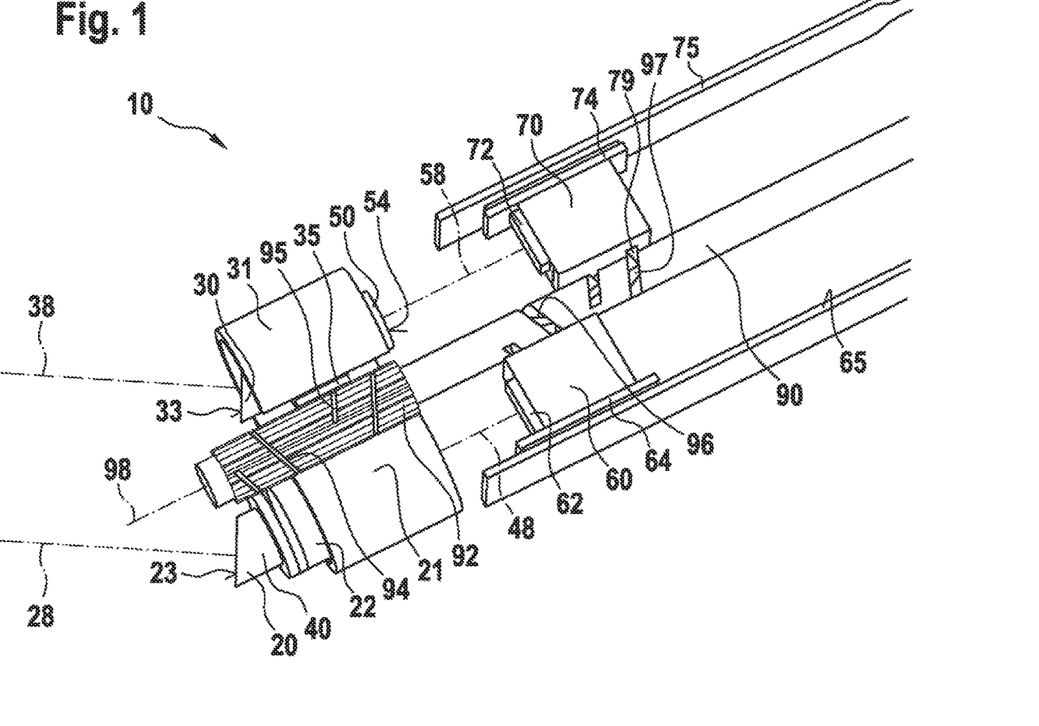
FIG. 1 shows a schematic axonometric illustration of a distal part of an apparatus for capturing a stereo image.

FIG. 1 shows a schematic axonometric illustration of a distal part of an apparatus 10 for capturing a stereo image. In particular, the apparatus 10 is a stereo endoscope or a stereo exoscope. The component parts of the apparatus 10 illustrated in FIG. 1 are enclosed by a hermetically sealed outer shaft, for example, which is not illustrated in FIG. 1 and which protects the component parts illustrated in FIG. 1 from environmental influences.

The apparatus 10 comprises a first viewing direction device 20 and a first objective 40, which form a unit in the illustrated example. The first viewing direction device 20 and the first objective 40 are held and fastened in a sleeve-shaped mount 22. The mount 22 is guided in a first guide 21 in such an interlocking manner that the mount 22, together with the first viewing direction device 20 and the first objective 40, rotates about the optical axis 48 of the first objective 40 and is displaceable within a predetermined range in the direction parallel to the optical axis 48 of the first objective 40.

The distal end of the first viewing direction device 20 is formed by a light entry face 23 which is inclined in relation to the optical axis 48 of the first objective 40. The first viewing direction device 20 bends or angles the first beam path formed by the first viewing direction device 20 and the first objective 40. The first beam path and the optical axis of the first beam path therefore have two different directions at the light entry face 23 of the viewing direction device 20 and at the light exit face of the viewing direction device. The optical axis 48 of the first objective 40 is the optical axis of the first viewing direction device 20 and of the first beam path at the light exit face of the first viewing direction device 20. The optical axis 28 of the first viewing direction device 20 and of the first beam path at the light entry face 23 of the viewing direction device 20 is not parallel to the optical axis 48 of the first objective 40, but it is orthogonal to the light entry face 23 of the viewing direction device 20 in the illustrated example.

By way of example, the first viewing direction device 20 has a plurality of prisms made of optically transparent materials that are cemented together, light being reflected at their interfaces, in particular on account of total internal reflection. As a result of these reflections, the light that is incident on the light entry face 23 of the viewing direction device 20 in parallel with the optical axis 28 of the first viewing direction device at the light entry face 23 thereof, emerges from the first viewing direction device 20 in parallel with the optical axis 48 of the objective 40 and enters into the first objective 40.

The angle between the optical axis 28 of the first viewing direction device 20 at the light entry face 23 thereof and the optical axis 48 of the first objective 40 is unchangeable in the examples illustrated here. Alternatively, and deviating from the examples illustrated here, the angle may be adjustable.

The apparatus 10 further comprises a first image sensor component 60 having a first image sensor 64. In the illustrated example, the first image sensor component 60 further has a first prism 62 with a reflective face 63 and the first image sensor 64 is arranged parallel to the optical axis 48 of the first objective 40. The first image sensor 64 is connected to the distal end of a circuit board 65. The circuit board 65 can be partly or completely flexible and/or extend up to a proximal end of the apparatus 10, which is not illustrated in FIG. 1. In addition to the image sensor 64, further electronic components for amplifying, preparing, processing analog or digital image signals produced by the first image sensor 64 can be provided on the circuit board 65. Further, conductor tracks of the first circuit board 65 can facilitate a transmission of an image signal to the proximal end of the apparatus 10, which is not illustrated in FIG. 1.

The apparatus 10 further comprises a second viewing direction device 30 and a second objective 50 in a mount, which is not visible in FIG. 1, within a second guide 31. The second viewing direction device 30 having a light entry face 33, which forms the distal end thereof, and an optical axis 38 at the light entry face 33 has an identical construction to the first viewing direction device 20. The second objective 50 with a light exit face 54 and an optical axis 58 has an identical construction to the first objective 40. The second viewing direction device 30 and the second objective form a second beam path. The guide 31 for the mount, which is not visible in FIG. 1, of the second viewing direction device 30 and of the second objective 50 is arranged in a mirror symmetric fashion or in approximately a mirror symmetric fashion in relation to the guide 21 of the mount 22 of the first viewing direction device 20 and of the first objective 40 in the outer shaft, which is not illustrated in FIG. 1.

The apparatus 10 further comprises a second image sensor component 70 having a second prism and a second image sensor 74, which is connected to the distal end of a second circuit board 75. In particular, the second image sensor component 70 has an identical construction to the first image sensor component 60 and it is arranged in a mirror symmetric fashion or in a substantially mirror symmetric fashion in relation to the latter in the illustrated example.

The apparatus 10 further comprises a drive shaft 90 having a gear 92 at the distal end of the drive shaft 90. The drive shaft 90 is rotatable about the longitudinal axis 98 thereof. The longitudinal axis 98 of the drive shaft 90 is parallel to the optical axes 48, 58 of the objectives 40, 50. The gear 92 at the distal end of the drive shaft 90 meshes with a gear that is formed by teeth at the outer circumference of the mount 22 of the first viewing direction device 20 and of the first objective 40 and that is covered in FIG. 1 by the assigned guide 21, and with a gear 35 that is formed by teeth at the outer circumference of the mount, incidentally not visible in FIG. 1, of the second viewing direction device 30 and of the second objective 50.

Therefore, a rotation of the drive shaft 90 brings about a simultaneous rotation of the viewing direction devices 20, 30 and of the objectives 40, 50 about the optical axes 48, 58 of the objectives 40, 50. The gears 35 at the outer circumferences of the mounts 22 of the viewing direction devices 20, 30 and of the objectives 40, 50 have the same diameter and the same number of teeth. Each rotation of the drive shaft 90 brings about a simultaneous rotation, in the same direction, of the two viewing direction devices 20, 30 and hence of the optical axes 28, 38 of the viewing direction devices 20, 30 at the light entry faces 23, 33 thereof.

Further, a plurality of guide grooves 94, 95, 96, 97 are provided in the outer surface of the drive shaft 90, said guide grooves each having a helical embodiment in the simplified example illustrated in FIG. 1. The first guide groove 94 and the second guide groove 95 are formed in the region of the gear 92 at the distal end of the drive shaft 90 and are wound in opposite directions. A sensing device, not visible in FIG. 1, in the form of a stylus coupled to the mount 22 of the first viewing direction device 20 and of the first objective 40 engages in the first guide groove 94 in the drive shaft 90. A sensing device in the form of a stylus, not visible in FIG. 1, coupled to the mount of the second viewing direction device 30 and of the second objective 50 engages in the second guide groove 95 in the drive shaft 90.

A third guide groove 96 and a fourth guide groove 97 are arranged in the vicinity of the image sensor components 60, 70 in the drive shaft 90. In the simplified example illustrated in FIG. 1, the third guide groove 96 and the fourth guide groove 97 each are helical and have opposite winding directions. A stylus, not visible in FIG. 1, at the first image sensor component 60 engages in the third guide groove 96.

A stylus 79 at the second image sensor component 70 engages in the fourth guide groove 97.

The winding directions and the leads of the first guide groove 94 and of the third guide groove 96 are the same. The winding directions and leads of the second guide groove 95 and of the fourth guide groove 97 are the same. Therefore, each rotation of the drive shaft 90 has as a consequence a synchronous, i.e. in the same direction and with the same speed, translational movement of the first viewing direction device 20, of the first objective 40, and of the first image sensor component 60 and an opposite, but amongst themselves synchronous, i.e. in the same direction and with the same speed, translational movement of the second viewing direction device 30, of the second objective 50, and of the second image sensor component 70. As mentioned, the meshing gears 92, 35 further cause each rotation of the drive shaft 90 to be accompanied by a synchronous rotation of the first viewing direction device 20, of the second viewing direction device 30, and hence also of the optical axes 28, 38 of the viewing direction devices 20, 30 at the light entry faces 23, 33 thereof (and, furthermore, this is accompanied by a rotation of the objectives 40, 50, but this is optically irrelevant). Therefore, the rotation of the viewing direction devices 20, 30 is coupled to a translational movement of the objectives 40, 50 and of the image sensor components 60, 70.

In particular, the guide grooves 94, 95, 96, 97 are embodied in such a way that the light entry faces 23, 33 of the viewing direction devices 20, 30 lie in a single plane orthogonal to the viewing direction in each viewing direction, i.e. in each orientation of the optical axes 28, 38 of the viewing direction devices 20, 30 at the light entry faces 23, 33 thereof. To this end and, in particular, deviating from the illustration in FIG. 1, the guide grooves 94, 95, 96, 97 are not helical in the true sense (i.e., with a constant gradient in each case) but have varying gradients. In particular, the gradients of the guide grooves 94, 95, 96, 97 at the locations at which the styluses 79 engage in the guide grooves 94, 95, 96, 97 are zero if, as indicated in FIG. 1, the optical axes 48, 58 of both objectives 40, 50 and the optical axes 28, 38 of the two viewing direction devices 20, 30 at the light entry faces 23, 33 thereof lie in a single plane.

Figure 2:
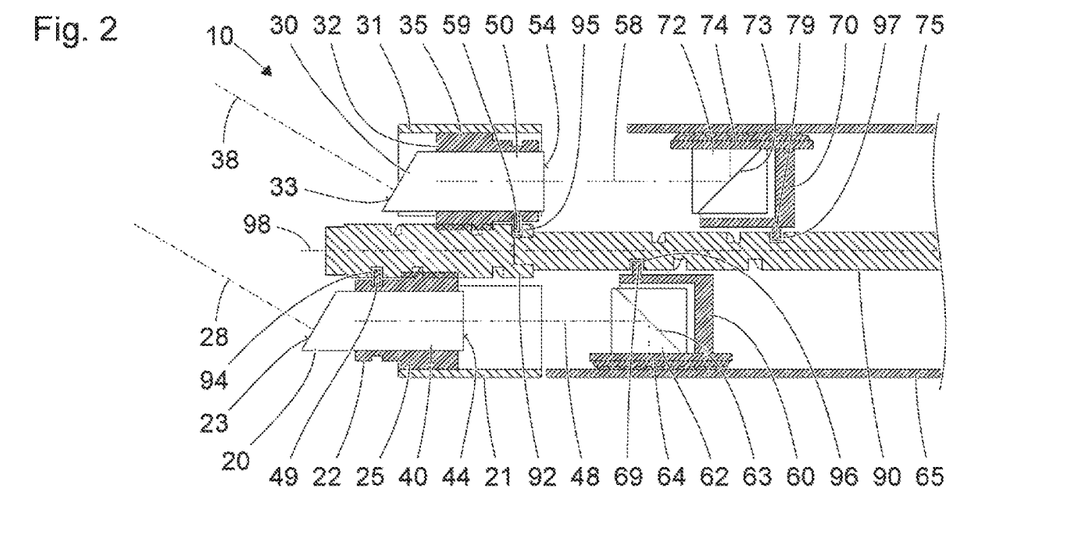
FIG. 2 shows a further schematic sectional illustration of the distal part of the apparatus from FIG. 1.

FIG. 2 shows a schematic sectional illustration of the distal part of the apparatus 10 from FIG. 1. The sectional plane of FIG. 2 contains the optical axes 48, 58 of the objectives 40, 50 and the optical axes 28, 38 of the viewing direction devices 20, 30 at the light entry faces 23, 33 thereof. Cut surfaces of optically transparent components, in particular of the viewing direction devices 20, 30, of the objectives 40, 50, and of the prisms 62, 72, are illustrated without hatching. Cut surfaces of all of the other components are illustrated with hatching.

In FIG. 2, both the mount 22 of the first viewing direction device 20 and of the first objective 40 and the mount 32 of the second viewing direction device 30 and of the second objective 50 as well as the gears 25, 35 at the mounts 22, 32 are visible. Further, the styluses 49, 59 at the mounts 22, 32 and hence at the viewing direction devices 20, 30 and at the objectives 40, 50 are visible.

In order to avoid a rotation of the styluses 49, 59 together with the mounts 22, 32 and hence in order to avoid a loss of the engagement of the styluses 49, 59 in the guide grooves 94, 95, each stylus 49, 59 is, in particular, part of a component, incidentally not visible in FIG. 2, which engages firstly in a circumferential groove of the assigned mount 22, 32 and secondly in a longitudinal groove of the assigned guide 21, 31 such that the styluses 49, 59 can only be moved parallel to the plane of the drawing of FIG. 2.

It is clear from FIG. 2 that the mounts 22, 32 do not have a symmetric embodiment in relation to one another and the styluses 49, 59 are arranged at opposite ends of the mounts 22, 32. As a result of this, it is possible to avoid an overlap between the first guide groove 94 for the first stylus 49 at the mount 22 of the first viewing direction device 20 and of the first objective 40 and the second guide groove 95 for the second stylus 59 at the mount 32 of the second viewing direction device 30 and of the second objective 50.

Further, reflecting faces 63, 73 are visible in the prisms 62, 72 in FIG. 2. Just like the light-sensitive faces of the image sensors 64, 74, the reflecting faces 63, 73 are orthogonal to the sectional plane of FIG. 2.

Further, the third stylus 69 of the first image sensor component 60, said third stylus engaging in the third guide groove 96, and the fourth stylus 79 of the second image sensor component 70, said fourth stylus engaging in the fourth guide groove 97 in the drive shaft 90, are visible in FIG. 2.

Figure 3:
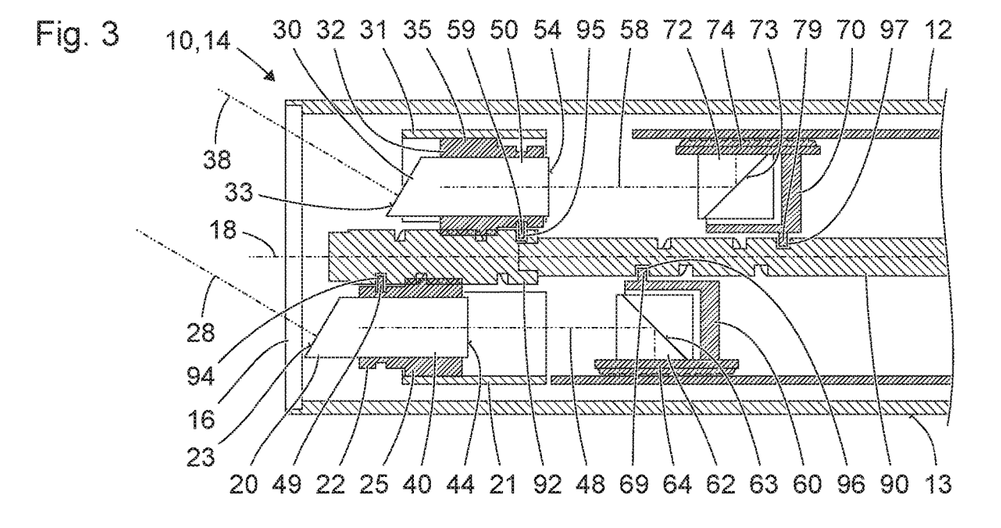
FIG. 3 shows a further schematic sectional illustration of the distal part of the apparatus from FIGS. 1 and 2.

FIG. 3 shows a further schematic illustration of a longitudinal section of the distal part of the apparatus 10 from FIGS. 1 and 2. The sectional plane of FIG. 3 corresponds to the sectional plane of FIG. 2. The configuration illustrated in FIG. 3 corresponds to the configuration illustrated in FIGS. 1 and 2.

The illustration in FIG. 3 differs from the illustrations in FIGS. 1 and 2 by virtue of, further, a shaft or outer shaft 12 of the apparatus 10 being illustrated. The shaft 12 has a substantially circular cylindrical design, and so its outer surface has a circular cylindrical region 13 (also referred to as a lateral face) with an axis of symmetry 18.

An optically transparent window component 16 is provided at the distal end 14 of the shaft 12. The viewing direction devices 20, 30 are arranged immediately proximal to the optically transparent window component 16. In the most distal position of the first viewing direction device 20, illustrated in FIG. 3, the light entry face thereof only has a small safety distance from the inner surface of the optically transparent window component 16.

Figure 4:
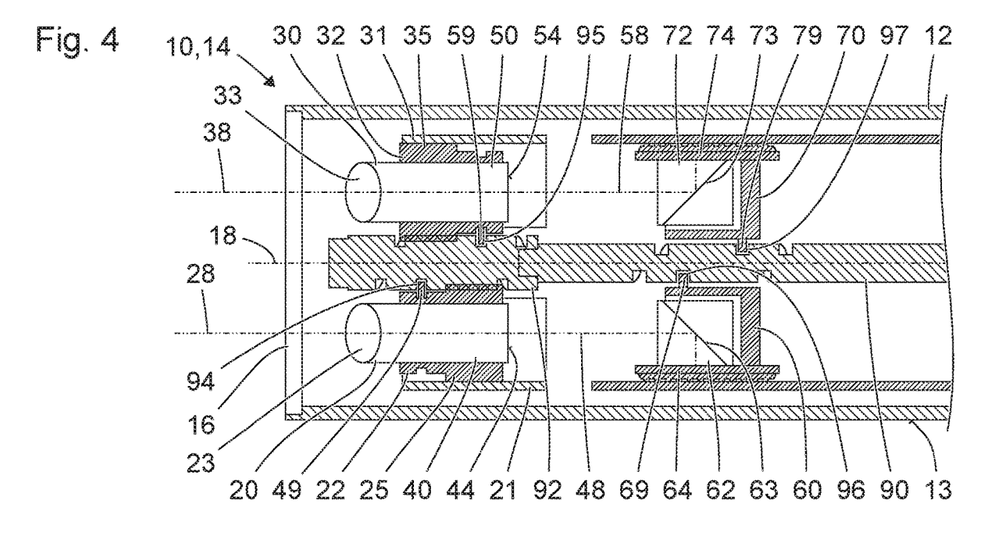
FIG. 4 shows a further schematic sectional illustration of the distal part of the apparatus from FIGS. 1 to 3.

FIG. 4 shows a further schematic illustration of a section through the distal part of the apparatus 10 from FIGS. 1 to 3. The sectional plane in FIG. 4 corresponds to the sectional planes in FIGS. 2 and 3. The type of illustration of FIG. 4 corresponds to that of FIG. 3; i.e., the shaft 12 with the optically transparent window component 16 is also illustrated.

The configuration shown in FIG. 4 differs from the configurations illustrated in FIGS. 1 to 3 in that the viewing direction devices 20, 30 (and hence also the objectives 40, 50) have different rotational and translational positions and the image sensor components 60, 70 have different translational positions. In the configuration shown in FIG. 4, the optical axes 28, 38 of the viewing direction devices 20, 30 at the light entry faces 23, 33 thereof include maximum (and, among themselves, the same) angles with the sectional plane of FIG. 4. Both the plane containing the optical axis of the first beam path (i.e., the optical axis 28 of the first viewing direction device 20 at the light entry face 23 thereof and the optical axis 48 of the first objective 40) and the plane containing the optical axis of the second beam path (i.e., the optical axis 38 of the second viewing direction device 30 at the light entry face 33 thereof and the optical axis 58 of the second objective 50) are each orthogonal to the sectional plane of FIG. 4 and hence orthogonal to the plane in which the optical axes 48, 58 of the objectives 40, 50 lie.

If, proceeding from the configuration shown in FIG. 4, the drive shaft 90 is rotated further in the same direction, a configuration which is mirror symmetrical to the configuration illustrated in FIG. 3 is obtained.

Figure 5:
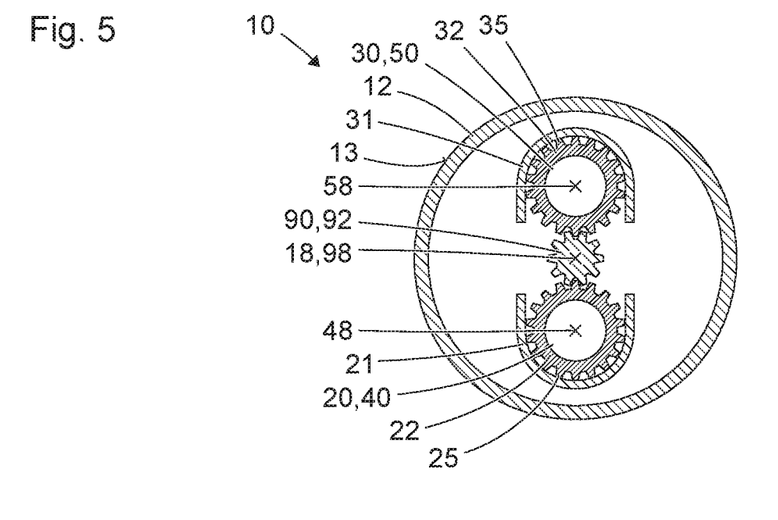
FIG. 5 shows a further schematic sectional illustration of the apparatus from FIGS. 1 to 4.

FIG. 5 shows a further schematic illustration of a section through the distal part of the apparatus 10 illustrated on the basis of FIGS. 1 to 4. The sectional plane of FIG. 5 is orthogonal to the sectional planes of FIGS. 2 to 4, orthogonal to the axis of symmetry 18 of the circular cylindrical region 13 of the outer surface of the shaft 12, and orthogonal to the optical axes 48, 58 of the objectives 40, 50. The sectional plane extends through the gear 92 at the distal end of the drive shaft 90 and through the gears 25, 35 at the mounts 22, 32 of the viewing direction devices 20, 30 and of the objectives 40, 50.

The U-shaped cross section of each guide 21, 31 can be seen in FIG. 5. The guides 21, 31 guide the mounts 22, 32 with little play or friction, wherein, in particular, the ends of the teeth of the gears 25, 35 abut against the inner surfaces of the guides 21, 31. The guides 21, 31 are open toward the drive shaft 90, and so the gear 92 at the distal end of the drive shaft 90 can mesh with the gears 25, 35 at the mounts 22, 32.

Figure 6:
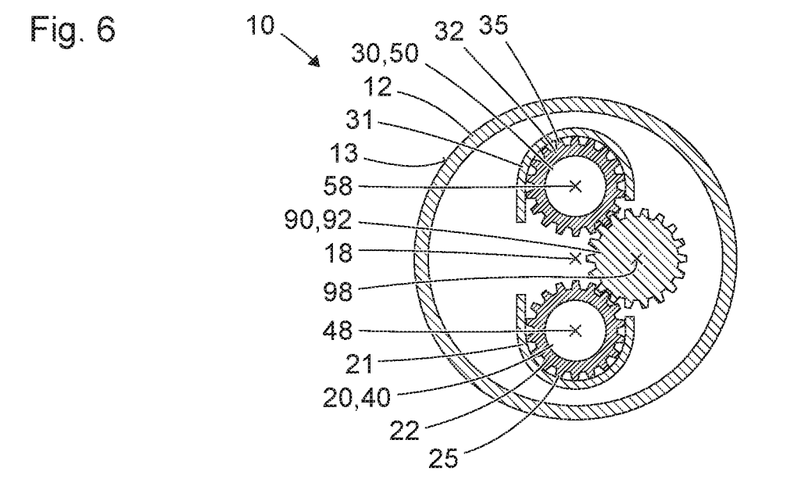
FIG. 6 shows a schematic sectional illustration of a further apparatus for capturing a stereo image.

FIG. 6 shows a schematic illustration of a section through the distal part of a further apparatus 10, which, in terms of some features, properties, and functions, is similar to the apparatus presented on the basis of FIGS. 1 to 5. The type of illustration, in particular the sectional plane of FIG. 6, corresponds to that of FIG. 5.

In particular, the apparatus 10 shown in FIG. 6 differs from the apparatus presented on the basis of FIGS. 1 to 5 in that the drive shaft 90 and the gear 92 at the distal end of the drive shaft 90 are not arranged exactly between the mounts 22, 32 for the viewing direction devices 20, 30 and the objectives 40, 50. Instead, the drive shaft 90 and the gear 92 at the distal end of the drive shaft 90 are arranged with lateral offset. Therefore, the drive shaft 90 and the gear 92 at the distal end of the drive shaft 90 are not rotated about the axis of symmetry 18 of the circular cylindrical region 13 of the outer surface of the shaft 12.

The eccentric arrangement of the drive shaft 90 indicated in FIG. 6 can—deviating from the illustration in FIG. 6—facilitate, for example, larger cross sections of the beam paths, in particular of the viewing direction devices 20, 30 and of the objectives 40, 50.

Figure 7:
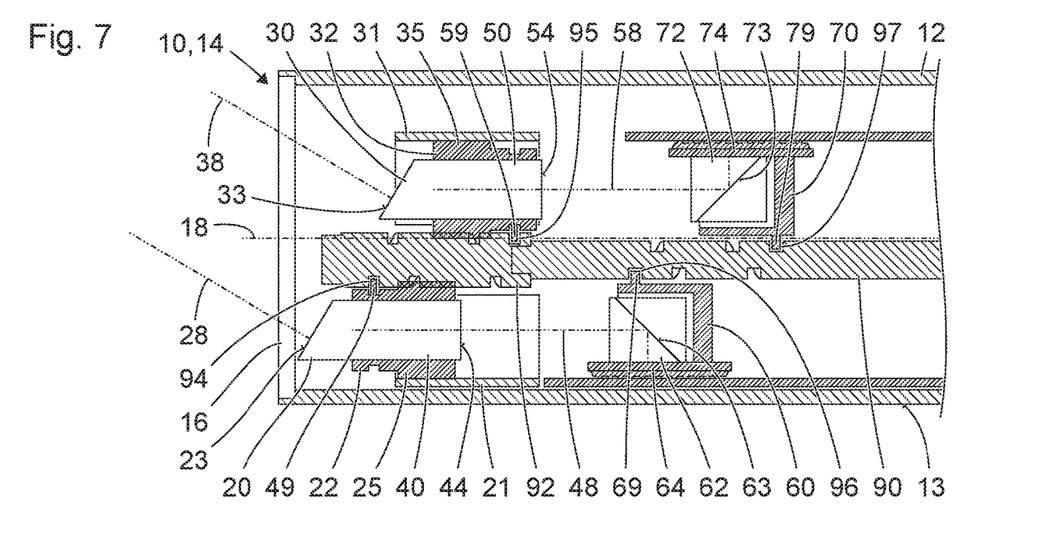
FIG. 7 shows a schematic sectional illustration of a distal part of a further apparatus for capturing a stereo image.

FIG. 7 shows a schematic illustration of a section through a distal part of a further apparatus 10, which, in terms of some features, properties, and functions, is similar to the apparatuses presented on the basis of FIGS. 1 to 6. The type of illustration, in particular the sectional plane, corresponds to that of FIGS. 2 to 4. The configuration shown in FIG. 7, in particular the orientation of the optical axes 28, 38 of the viewing direction devices 20, 30 at the light entry faces 23, 33 thereof, corresponds to the configuration shown in FIGS. 1 to 3. In particular, both the optical axes 48, 58 of the objectives 40, 50 and the optical axes 28, 38 of the viewing direction devices 20, 30 at the light entry faces 23, 33 thereof lie in the sectional plane of FIG. 7.

The apparatus 10 shown in FIG. 7 differs from the apparatuses presented on the basis of FIGS. 1 to 6 by, in particular, an asymmetric arrangement of the viewing direction devices 20, 30, of the objectives 40, 50, of the image sensor components 60, 70, and of the drive shaft 90 in relation to the axis of symmetry 18 of the circular cylindrical region 13 of the outer surface of the shaft 12. This asymmetric arrangement can prevent or reduce shadowing of the image captured by the second image sensor component 70 by the edge of the window component 16. The asymmetric arrangement shown in FIG. 7 may be permanently present or only present in the configuration shown in FIG. 7.

Figure 8:
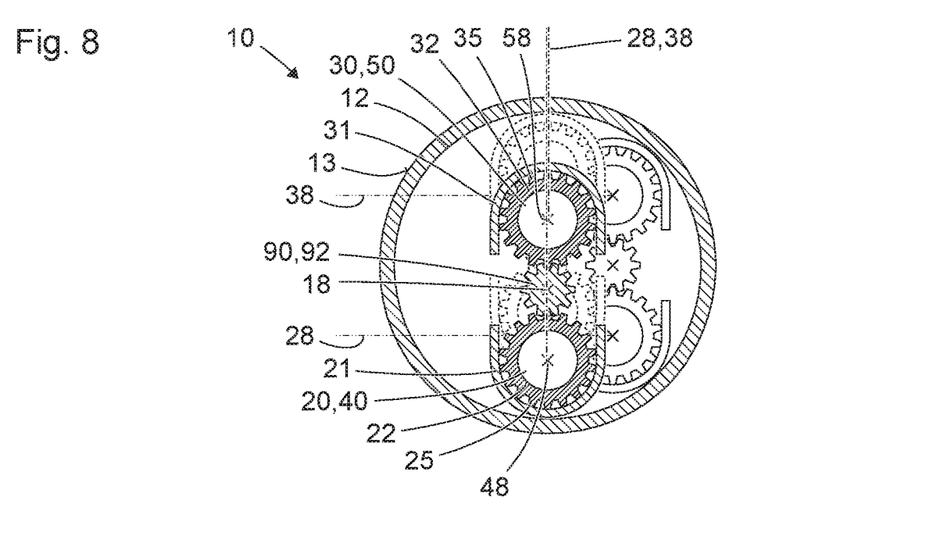
FIG. 8 shows a further schematic sectional illustration of the apparatus from FIG. 7.

FIG. 8 shows a further schematic illustration of a section through the distal part of the apparatus 10 from FIG. 7. The type of illustration, in particular the position and orientation of the sectional plane in FIG. 8, corresponds to that of FIGS. 5 and 6.

By way of full lines and hatched cut surfaces, FIG. 8 shows the configuration illustrated in FIG. 7. In this configuration, the optical axes 28, 38 of the viewing direction devices 20, 30 at the light entry faces 23, 33 thereof point to the upper edge of the sheet.

An opposite configuration is indicated using dashed lines and without hatching of the cut surfaces; here, the optical axes (not illustrated) of the viewing direction devices 20, 30 at the light entry faces thereof point in the opposite direction to the lower edge of the sheet. By way of a device that is not illustrated in FIGS. 7 and 8, the viewing direction devices 20, 30, the objectives 40, 50, the guides 21, 31, and the image sensor components 60, 70 can be moved between these two extreme positions depending on the viewing direction set. In particular, the movement can be effectuated along a straight path.

Alternatively, the movement may be effectuated along a curved path, and so a further configuration, illustrated in FIG. 8 using solid lines but no hatched cut surfaces, may be present between the two described extreme positions. In this configuration, the optical axes 28, 38 of the viewing direction devices 20, 30 at the light entry faces thereof point toward the left edge of the sheet and the viewing direction devices 20, 30, the objectives 40, 50, the guides 21, 31, and the image sensor components are displaced toward the right edge.

Figure 9:
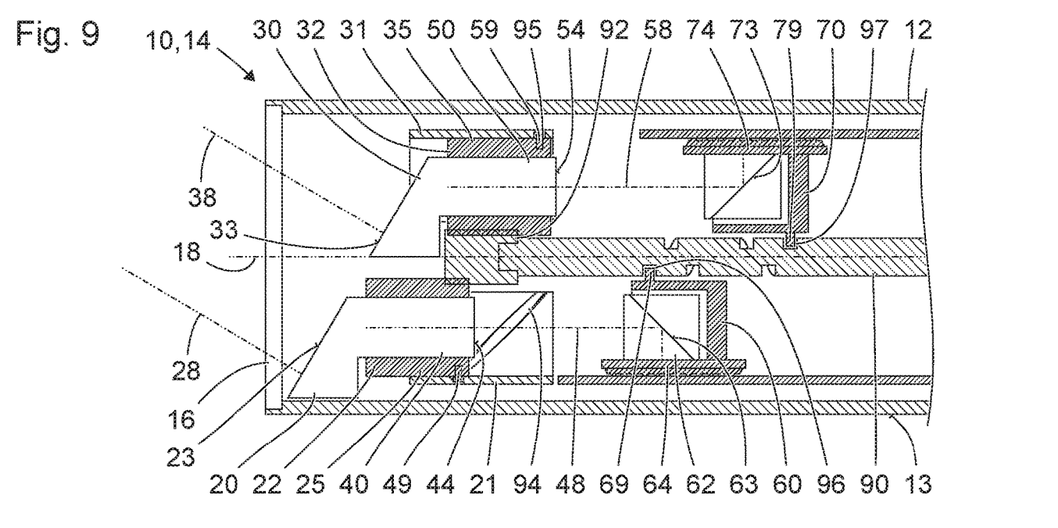
FIG. 9 shows a schematic sectional illustration of a distal part of a further apparatus for capturing a stereo image.

FIG. 9 shows a schematic illustration of a section through the distal part of a further apparatus 10, which, in terms of some features, properties, and functions, is similar to the apparatus presented on the basis of FIGS. 1 to 8, in particular the apparatus presented on the basis of FIGS. 1 to 5. The sectional plane of FIG. 9 corresponds to the sectional plane of FIGS. 2, 3, 4 and 7; the illustrated configuration corresponds to that of FIGS. 1 to 3 and 7.

The apparatus 10 shown in FIG. 9 differs from the apparatus presented on the basis of FIGS. 1 to 5 by virtue of, in particular, a different configuration of the viewing direction devices 20, 30. In particular, the viewing direction devices 20, 30 of the apparatus shown in FIG. 9 are embodied in such a way that the point of intersection of the optical axes 28, 38 of the viewing direction devices 20, 30 with the light entry faces 23, 33 thereof are significantly offset in relation to the optical axes 48, 58 of the objectives 40, 50. In particular, the point of intersection of the optical axes 28, 38 of each viewing direction device 20, 30 with the light entry face 23, 33 thereof lies outside of the cross sections of the objectives 40, 50 in relation to a projection parallel to the optical axes 48, 58 of the objectives 40, 50.

This can prevent or reduce shadowing—in particular shadowing of the image captured by the second image sensor component 70 in the configuration shown in FIG. 9—by the edge of the optically transparent window component 16.

The apparatus 10 shown in FIG. 9 differs further from the apparatus presented on the basis of FIGS. 1 to 5 in that styluses 49, 59 at the mounts 22, 32 do not engage in grooves in the drive shaft 90 or the gear 92, but in grooves 94, 95 in the guides 21, 31.

Figure 10:
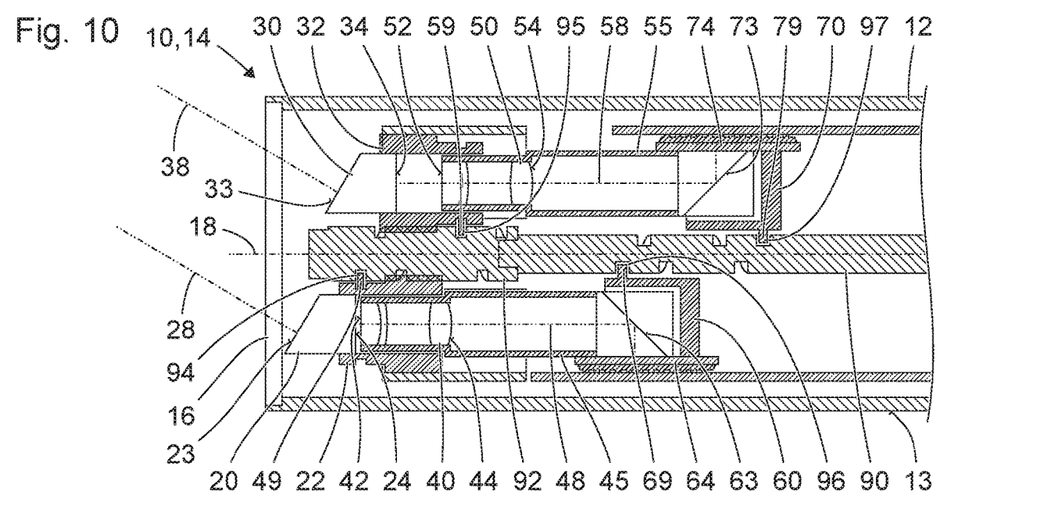
FIG. 10 shows a schematic sectional illustration of a distal part of a further apparatus for capturing a stereo image.

FIG. 10 shows a schematic illustration of a section through the distal part of a further apparatus 10 which, in terms of some features, properties, and functions, is similar to the apparatuses presented on the basis of FIGS. 1 to 9. The type of the illustration, in particular the sectional plane in FIG. 10, corresponds to that of FIGS. 2, 3, 4, 7 and 9. The shown configuration corresponds to the configuration shown in FIGS. 1 to 3, 7 and 9.

The apparatus 10 shown in FIG. 10 differs from the apparatuses presented on the basis of FIGS. 1 to 9 by virtue of, in particular, the viewing direction devices 20, 30 with the assigned objectives 40, 50 not forming integral components. Rather, the light exit faces 24, 34 of the viewing direction devices 20, 30 are not identical to the light entry faces 42, 52 of the objectives 40, 50; instead, they are spaced apart from the latter and clearly distinguishable in FIG. 10.

In the example shown in FIG. 10, only the first viewing direction device 20 is rigidly connected to the first mount 22 and only the second viewing direction device 30 is rigidly connected to the second mount 32. The first objective 40 is rigidly connected to the first image sensor component 60 by way of a first tube 45. The second objective 50 is connected in a mechanically rigid fashion to the second image sensor component 70 by way of a second tube 55. However, as indicated in FIG. 10, the distal ends of the tubes 45, 55, and hence the objectives 40, 50, may be guided in the mounts 22, 32 with little play and friction.

The independent control of the translation of the viewing direction devices 20, 30, indicated in FIG. 10, can be used in order, as indicated in FIG. 10, to displace the viewing direction devices 20, 30 to a less pronounced extent than the objectives 40, 50 and the image sensor components 60, 70. To this end, the first guide groove 94 and the second guide groove 95, in particular, have different, namely smaller, gradients and leads than the third guide groove 96 and the fourth guide groove 97. A consequence of the differently pronounced displacement of the viewing direction devices 20, 30 on the one hand and of the objectives 40, 50 is that the distance between the light exit face 24 of the first viewing direction device 20 and the light entry face 42 of the first objective 40, and the distance between the light exit face 34 of the second viewing direction device 30 and the light entry face 52 of the second objective 50, is not constant in each case but varies depending on the viewing direction. In the viewing direction indicated in FIG. 10, the distance between the light exit face 24 of the first viewing direction device 20 and the light entry face 42 of the first objective 40 differs from the distance between the light exit face 34 of the second viewing direction device 30 and the light entry face 52 of the second objective 50.

The independent control of the translation movement of the viewing direction devices 20, 30 can be used to prevent a variation of the distance of the optical axes 28, 38 of the viewing direction devices 20, 30 at the light entry faces 23, 33 thereof in the case of the rotation of the viewing direction. At the same time, it is possible to prevent or reduce the shadowing by the edge of the optically transparent window component 16.

Deviating from the illustration in FIG. 10, only part of the first objective 40 can be connected in a mechanically rigid fashion to the first tube 45 (and hence, ultimately, to the first image sensor component 60, too) and only part of the second objective 50 can be connected in a mechanically rigid fashion to the second tube 55 (and hence, ultimately, to the second image sensor component 70, too). In this case, in particular, the remainder of the first objective 40 is mechanically coupled or connected to, or integrated with, the first viewing direction device 20 and the remainder of the second objective 50 is mechanically coupled or connected to, or integrated with, the second viewing direction device 300. In particular, the objectives are respectively divided at a position at which the light emanating from an (ultimately sharply imaged) object is parallel such that a relative movement of the parts of each objective has no influence of the imaging, in particular on the sharpness of the imaging.

Features of the apparatuses presented on the basis of FIGS. 1 to 10 are combinable with one another. By way of example, the pronounced offset of the optical axes 28, 38 of the viewing direction devices 20, 30 at the light entry faces 23, 33 thereof in relation to the optical axes 48, 58 of the objectives 40, 50, indicated on the basis of FIG. 9, can be combined with the independent control of the translation of the viewing direction devices 20, 30, indicated in FIG. 10, in order to further reduce the shadowing by the edge of the optically transparent window component 16.

The invention claimed is:

1. An apparatus for capturing a stereo image, having:
   a first objective for producing a first image that is intended to be observed by a first eye of an observer;
   a second objective for producing a second image that is intended to be observed by a second eye of an observer;
   a first viewing direction device that is rotatable about a first axis of rotation and assigned to the first objective, the first axis of rotation being colinear with an optical axis of the first objective;
   a second viewing direction device that is rotatable about a second axis of rotation and assigned to the second objective, the second axis of rotation being colinear with an optical axis of the second objective;
   a first image sensor for capturing the first image;
   a second image sensor for capturing the second image; and
   a drive shaft that is rotationally coupled to the first viewing direction device and to the second viewing direction device;
   wherein a viewing direction of the apparatus is rotatable by way of a simultaneous rotation of the first viewing direction device about the first axis of rotation and the second viewing direction device about the second axis of rotation,
   wherein the first objective or part of the first objective is movable in a translational fashion,
   wherein a cam mechanism is provided and embodied to couple a rotation of the first viewing direction device to a translational movement of the first objective or of part of the first objective.

2. The apparatus according to claim 1, wherein the cam mechanism or a further cam mechanism is provided and embodied to couple a rotation of the first viewing direction device to a translational movement of the first viewing direction device in the direction in which the first objective or part of the first objective is movable.

3. The apparatus according to claim 1, wherein the cam mechanism or a further cam mechanism is provided and embodied to couple a rotation of the first viewing direction device to a translational movement of the first image sensor that is assigned to the first objective or to a light entry face of an image transmission device.

4. The apparatus according to claim 1, wherein the first objective includes a first part and a second part, wherein the apparatus is embodied in such a way that, either, only the translational movement of the first part is coupled to the rotation of the first viewing direction device or that a rotation of the first viewing direction device is accompanied by different translational movements of the first part and of the second part of the first objective.

5. The apparatus according to claim 1, wherein at least either the first viewing direction device and the second viewing direction device are in each case arranged, at least in part, next to the drive shaft, or the first objective and the second objective are in each case arranged, at least in part, next to the drive shaft.

6. The apparatus according to claim 1, wherein the drive shaft includes a cam carrier, which is a constituent part of the cam mechanism, or said drive shaft is rotationally coupled to a cam carrier, which is a constituent part of the cam mechanism, a cam, which is a constituent part of the cam mechanism, for coupling a rotation of the first viewing direction device to a translational movement of the first objective or part of the first objective being provided on an outer side of the cam carrier.

7. The apparatus according to claim 1, wherein the cam mechanism includes a groove or a web or a step at the drive shaft or at a cam carrier that is rotationally coupled to the drive shaft and a pin or a web or any other sensing device at the first objective or part of the first objective or at a component that is translationally coupled to the first objective or part of the first objective.

8. The apparatus according to claim 1, wherein the cam mechanism includes a groove or a web or a step at the first objective or part of the first objective or at a component that is translationally coupled to the first objective or part of the first objective and a sensing device at the drive shaft or at a component that is rotationally coupled to the drive shaft.

9. The apparatus according to claim 1, wherein the drive shaft is arranged between the first objective and the second objective.

10. An apparatus for capturing a stereo image, having:
    a first objective for producing a first image that is intended to be observed by a first eye of an observer;
    a second objective for producing a second image that is intended to be observed by a second eye of an observer;
    a first viewing direction device that is rotatable about a first axis of rotation and assigned to the first objective;
    a second viewing direction device that is rotatable about a second axis of rotation and assigned to the second objective;
    a first image sensor for capturing the first image;
    a second image sensor for capturing the second image; and
    a shaft having a distal end, wherein an outer lateral face of the shaft is rotationally symmetric in relation to an axis of symmetry, at least in a vicinity of the distal end of the shaft,
    wherein a viewing direction of the apparatus is rotatable by way of a simultaneous rotation of the first viewing direction device about the first axis of rotation and the second viewing direction device about the second axis of rotation,
    wherein the first objective or part of the first objective is movable in a translational fashion,
    wherein a cam mechanism is provided and embodied to couple a rotation of the first viewing direction device to a translational movement of the first objective or of part of the first objective;
    wherein the first viewing direction device, the second viewing direction device, the first objective and the second objective are arranged in the shaft,
    wherein at least in one viewing direction of the apparatus, a proximal portion of the optical axis of the first viewing direction device and a proximal portion of the optical axis of the second viewing direction device are not arranged mirror symmetrically in relation to a plane of symmetry that contains the axis of symmetry of the shaft.

11. The apparatus according to claim 1, further having:
a device for the translational movement of the viewing direction devices in a direction orthogonal to the axis of symmetry of the shaft, depending on a set viewing direction.

12. The apparatus according to claim 2, wherein the cam mechanism or a further cam mechanism is provided and embodied to couple a rotation of the first viewing direction device to a translational movement of the first image sensor that is assigned to the first objective or to a light entry face of an image transmission device.

13. The apparatus according to claim 2, wherein the first objective includes a first part and a second part, wherein the apparatus is embodied in such a way that, either, only the translational movement of the first part is coupled to the rotation of the first viewing direction device or that a rotation of the first viewing direction device is accompanied by different translational movements of the first part and of the second part of the first objective.

14. The apparatus according to claim 2, further having:
a drive shaft that is rotationally coupled to the first viewing direction device and to the second viewing direction device.

15. The apparatus according to claim 5, wherein the drive shaft includes a cam carrier, which is a constituent part of the cam mechanism, or said drive shaft is rotationally coupled to a cam carrier, which is a constituent part of the cam mechanism, a cam, which is a constituent part of the cam mechanism, for coupling a rotation of the first viewing direction device to a translational movement of the first objective or part of the first objective being provided on an outer side of the cam carrier.

16. The apparatus according to claim 5, wherein the cam mechanism includes a groove or a web or a step at the drive shaft or at a cam carrier that is rotationally coupled to the drive shaft and a pin or a web or any other sensing device at the first objective or part of the first objective or at a component that is translationally coupled to the first objective or part of the first objective.

17. The apparatus according to claim 5, wherein the cam mechanism includes a groove or a web or a step at the first objective or part of the first objective or at a component that is translationally coupled to the first objective or part of the first objective and a sensing device at the drive shaft or at a component that is rotationally coupled to the drive shaft.

18. An apparatus for capturing a stereo image, having:
a first objective for producing a first image that is intended to be observed by a first eye of an observer;
a second objective for producing a second image that is intended to be observed by a second eye of an observer;
a first viewing direction device that is rotatable about a first axis of rotation and assigned to the first objective;
a second viewing direction device that is rotatable about a second axis of rotation and assigned to the second objective;
a first image sensor for capturing the first image;
a second image sensor for capturing the second image; and
a shaft having a distal end, wherein an outer lateral face of the shaft is rotationally symmetric in relation to an axis of symmetry, at least in a vicinity of the distal end of the shaft,
wherein a viewing direction of the apparatus is rotatable by way of a simultaneous rotation of the first viewing direction device about the first axis of rotation and the second viewing direction device about the second axis of rotation,
wherein the first objective or part of the first objective is movable in a translational fashion,
wherein a cam mechanism is provided and embodied to couple a rotation of the first viewing direction device to a translational movement of the first objective or of part of the first objective;
wherein the cam mechanism or a further cam mechanism is provided and embodied to couple a rotation of the first viewing direction device to a translational movement of the first viewing direction device in the direction in which the first objective or part of the first objective is movable;
wherein the first viewing direction device, the second viewing direction device, the first objective and the second objective are arranged in the shaft,
wherein at least in one viewing direction of the apparatus, a proximal portion of the optical axis of the first viewing direction device and a proximal portion of the optical axis of the second viewing direction device are not arranged mirror symmetrically in relation to a plane of symmetry that contains the axis of symmetry of the shaft.

19. The apparatus according to claim 2, further having:
a device for the translational movement of the viewing direction devices in a direction orthogonal to the axis of symmetry of the shaft, depending on a set viewing direction.

* * * * *